United States Patent [19]
Moeinzadeh et al.

[11] Patent Number: 5,111,987

[45] Date of Patent: May 12, 1992

[54] SEMI-DISPOSABLE SURGICAL STAPLER

[76] Inventors: Manssour H. Moeinzadeh, 2012 Byrnebruk Rd., Champaign, Ill. 61821; Lawrence M. Kaplan, 1021 Arlington Blvd. #312E, Arlington, Va. 22209; Jeffrey A. Gurosh, 15031 Chicago Rd., Dolton, Ill. 60419

[21] Appl. No.: 522,583

[22] Filed: May 14, 1990

[51] Int. Cl.⁵ .............................................. A61B 17/04
[52] U.S. Cl. ..................................... 227/180; 227/19; 227/176; 606/219
[58] Field of Search ................... 227/19, 76, 144, 180, 227/181, 182, 176; 606/219, 142, 143

[56] References Cited

U.S. PATENT DOCUMENTS

| | | | |
|---|---|---|---|
| 4,520,817 | 6/1985 | Green | 227/180 |
| 4,633,861 | 1/1987 | Chow et al. | 227/180 |
| 5,014,899 | 5/1991 | Presty et al. | 227/180 |

Primary Examiner—Frank T. Yost
Assistant Examiner—Scott A. Smith
Attorney, Agent, or Firm—Lawrence M. Kaplan

[57] ABSTRACT

A semi-disposable surgical stapling instrument for the replacement of staple cartridges, as needed, in the course of an operation, and for the optional provision of a knife to cut tissue between staple rows. Propulsion of the stapling unit may be powered and controlled from the back of the instrument by either hand, as desired, during a surgical procedure with minimal generation of frictional or distorting forces. Economic materials of construction may be employed.

11 Claims, 5 Drawing Sheets

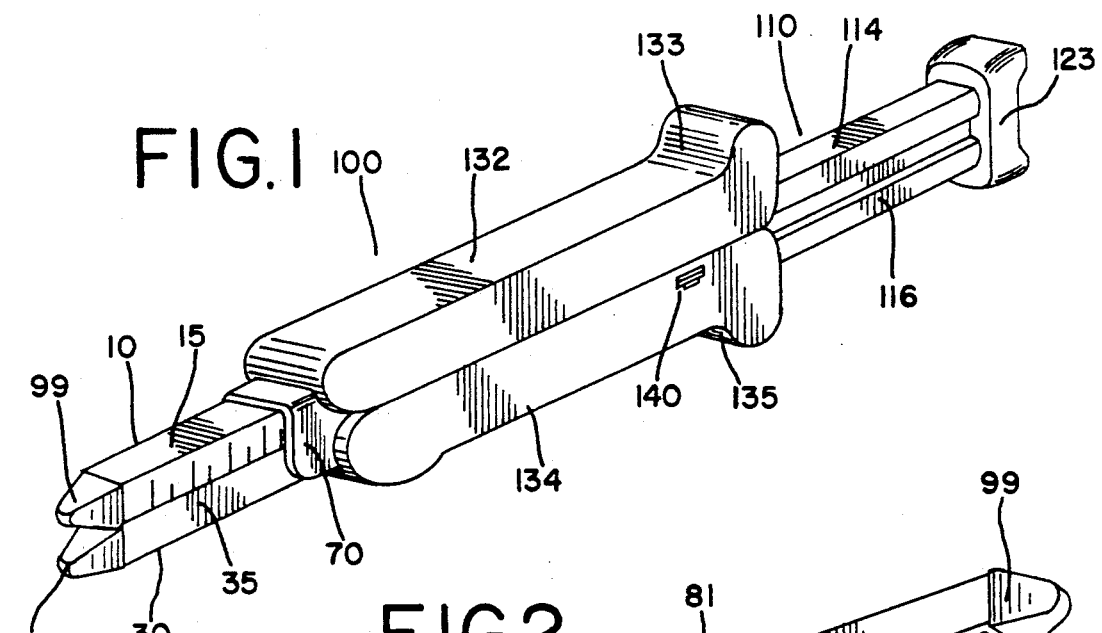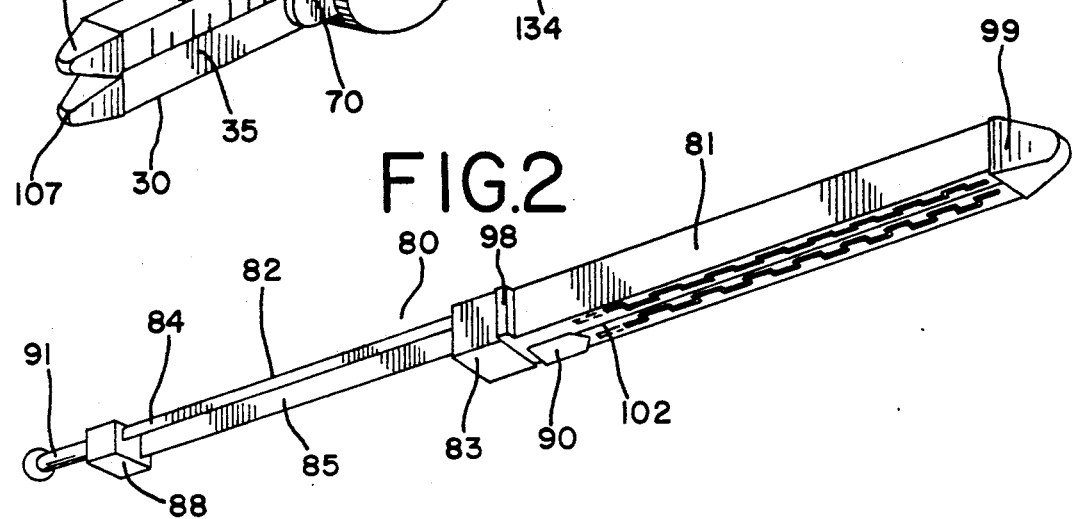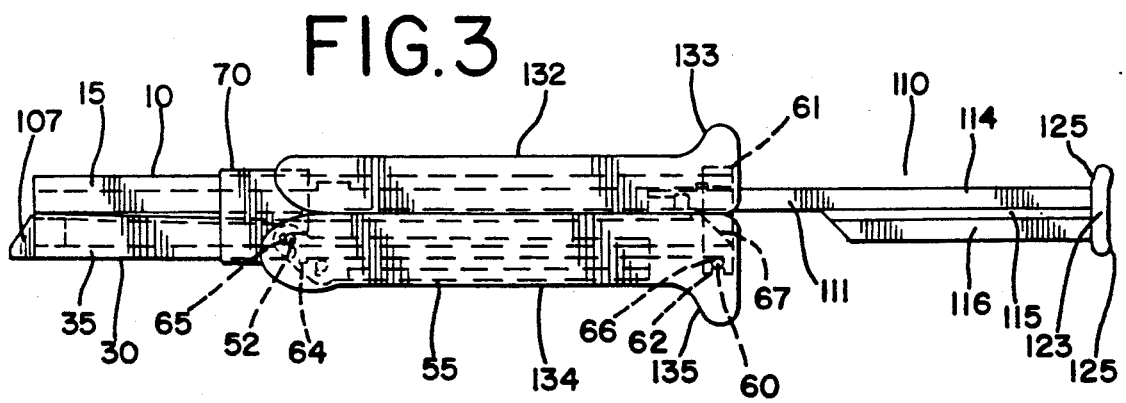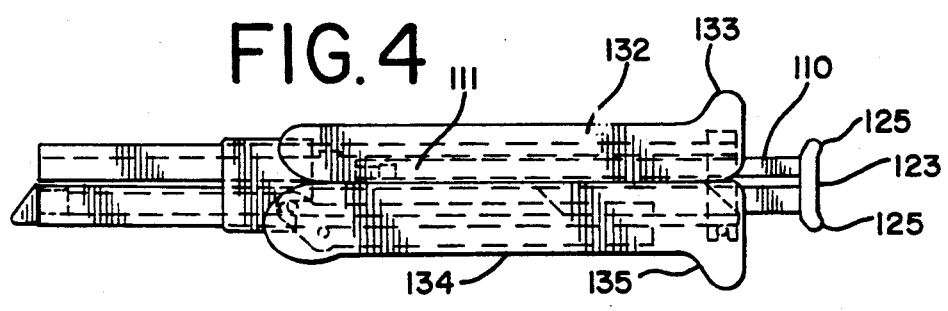

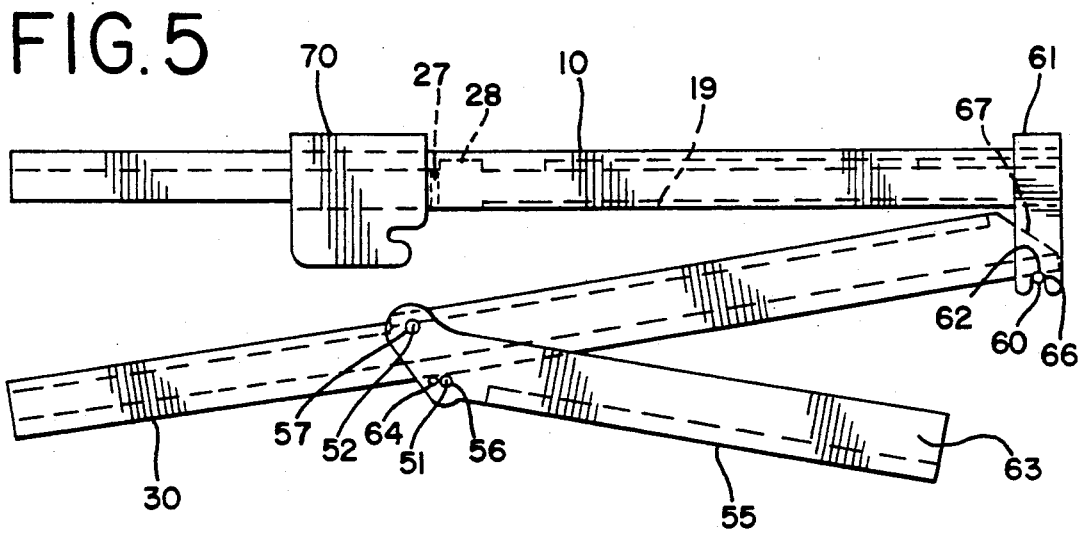
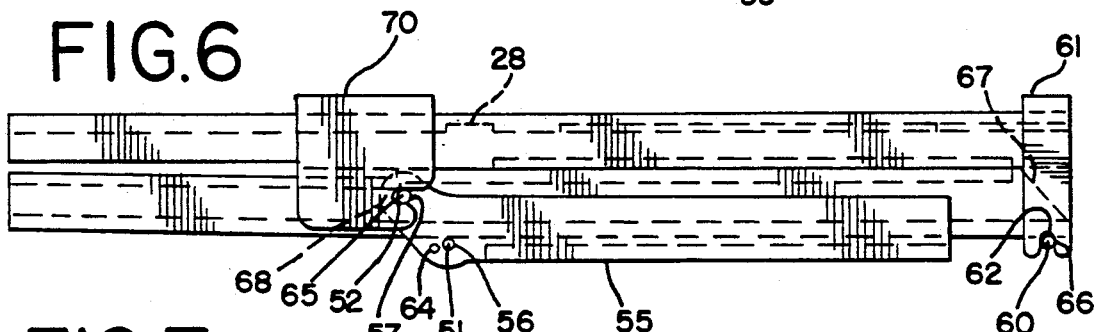
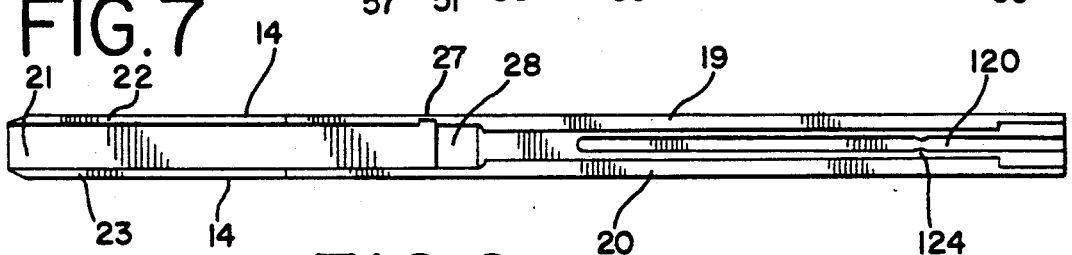
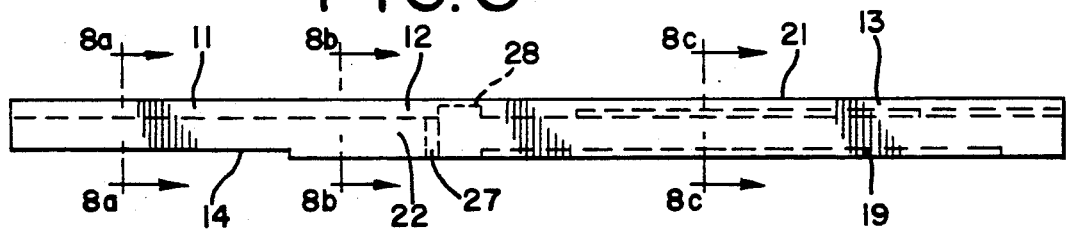
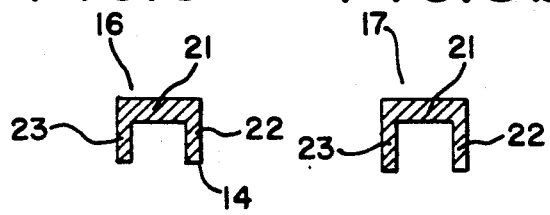
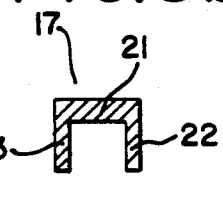
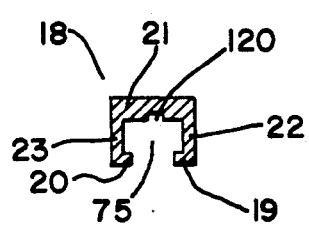

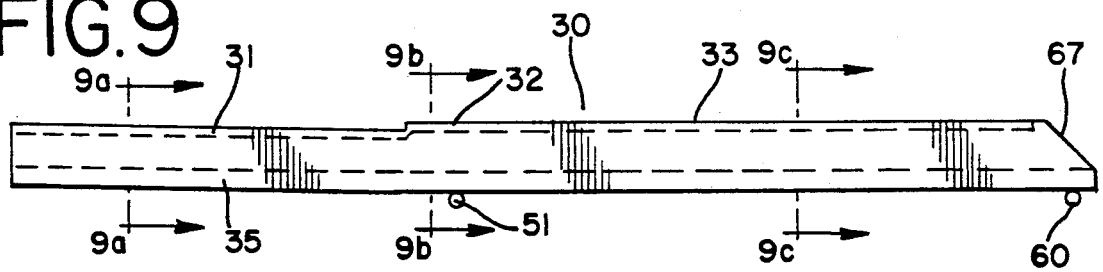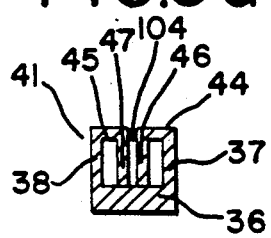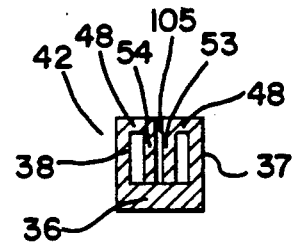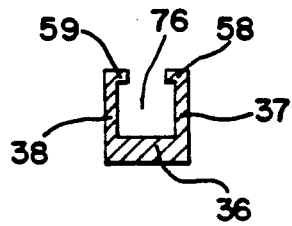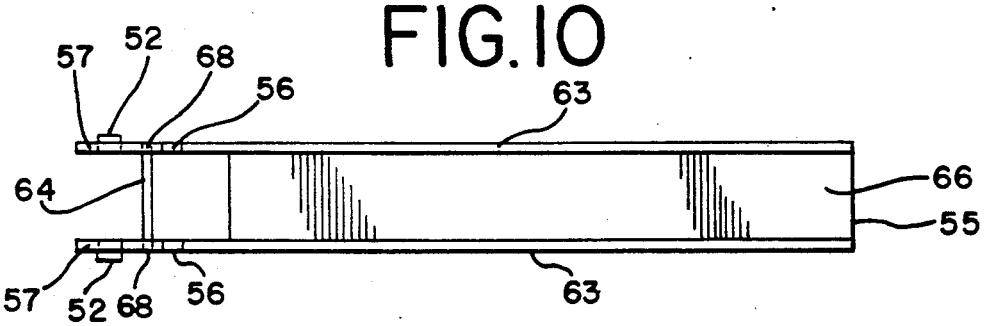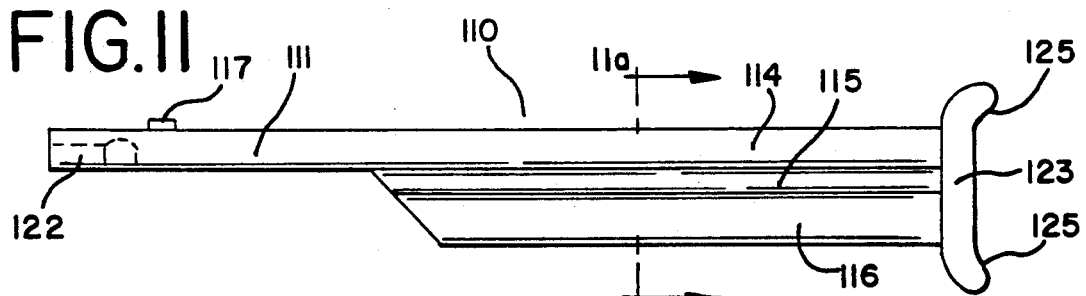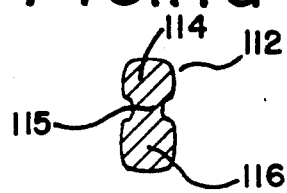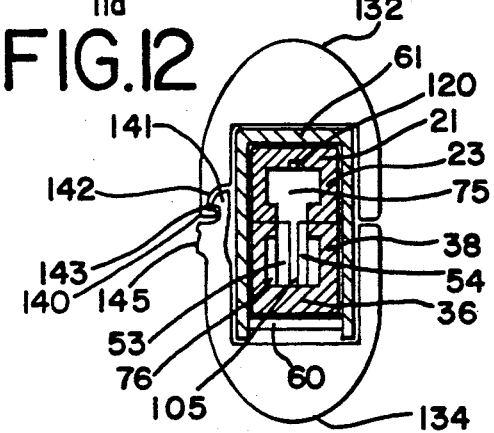

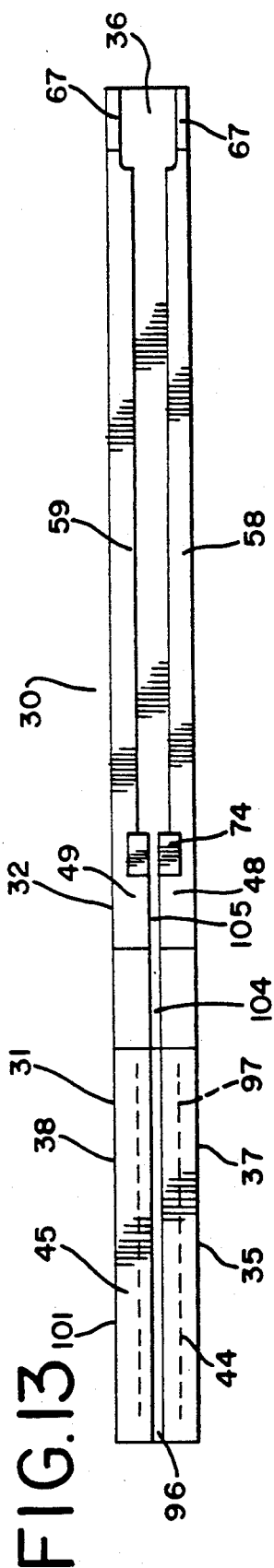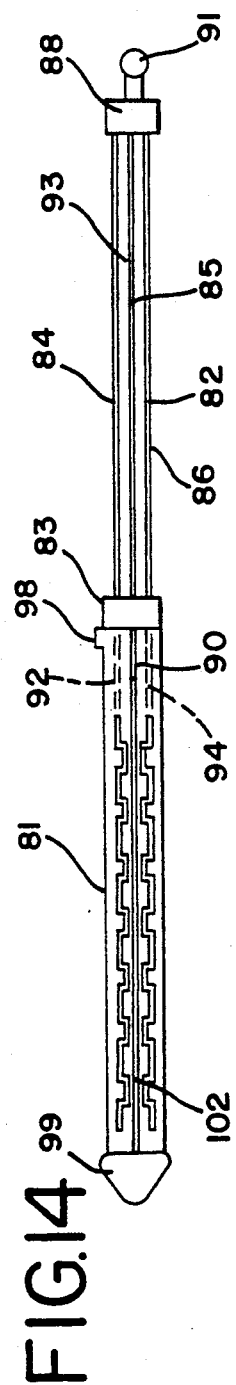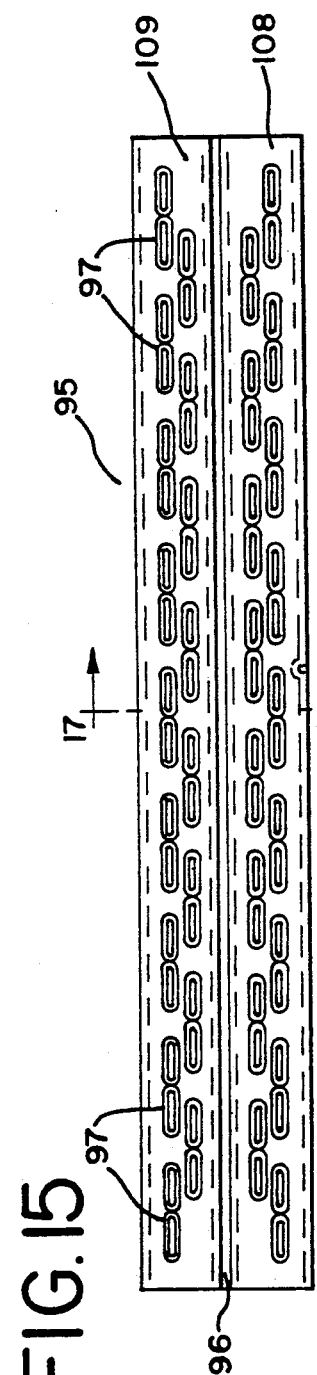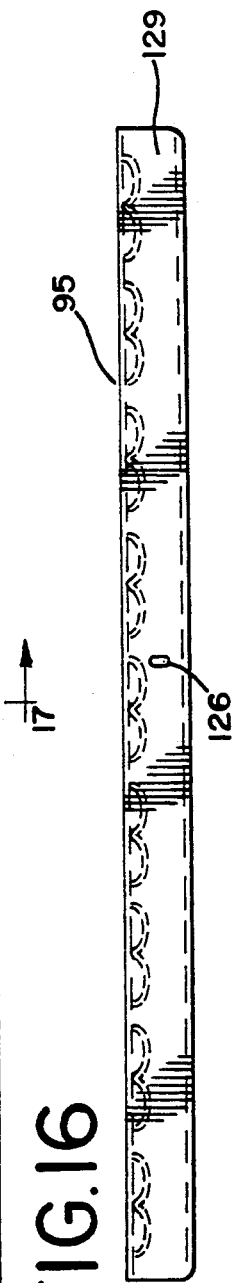

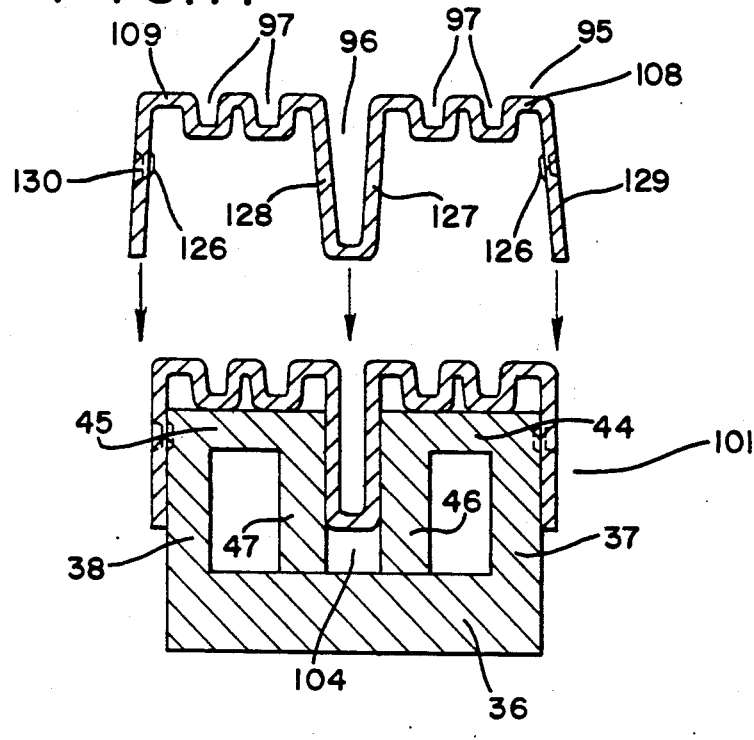
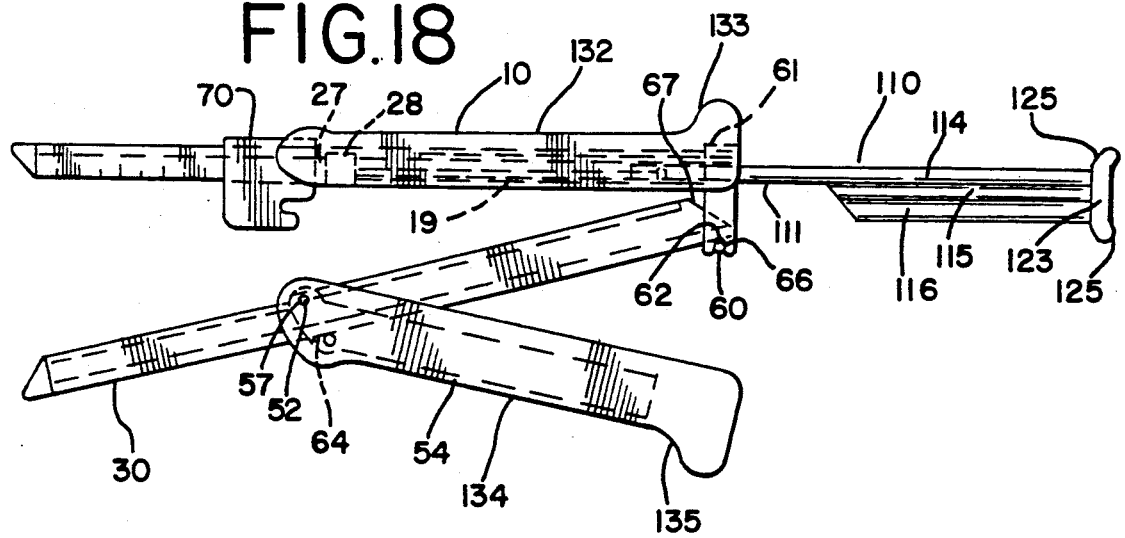

SEMI-DISPOSABLE SURGICAL STAPLER

CROSS-REFERENCES TO RELATED APPLICATIONS

This application is a continuation-in-part of the present inventors' abandoned application Ser. No. 300,387, filed Jan. 23, 1989, for SEMI-DISPOSABLE SURGICAL INSTRUMENT.

BACKGROUND OF THE INVENTION

1. Field of the Invention

This invention relates to a novel surgical stapling instrument, particularly useful in intralumenal anastomosis and characterized in affording semi-disposable properties. This invention particularly relates to a surgical stapling instrument employed in placing two or more evenly spaced, laterally aligned rows of staples in an internal organ during a surgical procedure.

Such instruments generally comprise two elongate jaw members, respectively affording a staple holder and an aligned anvil for closing the staples. The staple holder is designed to afford at least two rows of spaced staples on either side of a longitudinal opening in the anvil member. A slider assembly including a knife is provided to move longitudinally along the jaw members to eject and close staples while severing the tissue by passage of the knife through the longitudinal opening in the anvil member.

It is noted at the outset that the prior art sometimes uses the term "pusher bar" to describe what is herein referred to as the "slider assembly." We further note that the term "pusher bar" is herein used to describe a component of the disclosed invention that is distinctive from the "slider assembly."

2. Description of Related Art

In earlier prior art instruments, the staple holders, associated anvil members, and slider and knife assemblies have typically been constructed of disposable plastic materials and low-cost metals. Frame members of the instruments have been made of more durable materials suitable for sterilizing so that the instruments could be available for repeated use. By way of example, one instrument of this type is disclosed in U.S. Pat. No. 3,499,591, the disclosure of which is incorporated herein by reference.

More recent prior art instruments have been designed to be wholly disposable. This eliminates the need for repeated sterilization and insures that the instrument is ready for use without concern for necessary preparatory steps. Inasmuch as the instrument is to be discarded after one surgical operation, its design typically employs readily available, low-cost materials of construction to achieve an economically attractive result.

In such stapling instruments, large forces are generated when the tissue is clamped between the jaws, the staples are made to pass through the tissue, and the staples are closed in contact with aligned depressions in the anvil. These forces are of such a magnitude as to typically cause vertical separation and lateral distortion of the jaws and thus affect correct staple closure. Such forces become a primary concern when lighter materials are used, as, for example, in the design of the disposable instrument.

Earlier prior art instruments were designed to provide that the knife blade was an integral part of the sterilizable instrument so that the knife blade was resused when the unit was reloaded with staples for future use. With time, the knife blade became dulled by the repeated stapling procedures so that cuts were no longer as clean as with an unused blade.

More recent prior art, providing fully disposable surgical staplers, as suggested by U.S. Pat. No. 4,429,695, does not provide for replacement of the staple holder. Accordingly, the instrument must be abandoned after one firing process even though the operative surgical procedure may call for more staples or for more than one stapling operation. The need for a second instrument in a single patient's operation leads to more expensive procedures.

Further, support shoes which are carried by the slider and knife assemblies to provide vertical and lateral support to the jaws regularly encounter friction forces that make pushing difficult and do not permit the smooth, sliding action helpful to successful stapling procedure.

Recent prior art instrument designs generally require the use of a knife blade because the support shoes are connected to a plate member which passes through the tissue and thus must follow behind the knife blade. The support shoes in these prior art instruments restrain the jaws from vertical separation and lateral distortion.

In the prior art, the slider assembly (sometimes referred to as the "pusher bar" in the prior art) is designed to provide a thumb tab projecting laterally outward from between the upper and lower frame members on only one side of the instrument so that the propulsion of the pusher bar is effected by one hand laterally displaced from the longitudinal movement of the pusher bar. This action may place disorienting strains on the normal movement of the slider assembly and the instrument and may also affect the placement of the staples in the tissue.

There remains a need for an improved surgical stapler instrument, employing economic materials of construction, which can provide for the affording of sufficient staples to complete a patient's surgical operation, for the minimization of forces tending to hinder proper operation of the instrument, and for more convenient manipulation during the surgical operation procedure. Additionally, there remains a need for making the inclusion of a knife unit optional, as a matter of economy where one is not needed.

SUMMARY OF THE INVENTION

The invention of this disclosure provides a semi-disposable surgical stapling instrument wherein additional staples can be quickly and easily afforded by disposal of a spent staple cartridge assembly, comprising a staple holder and a slider assembly, and insertion of replacement staple cartridge assemblies, as may be required, during a surgical operation. The use of a knife blade, in conjunction with the stapler assembly, is optional.

This invention provides a surgical stapling instrument, employing economic materials of construction, having improved stability relative to frictional and dynamic forces.

This invention further provides a surgical stapling instrument that is resistant to premature, accidental staple ejection.

This invention also provides a surgical stapling instrument having jaws with minimized dimensions to facilitate insertion of the stapler jaws into the surgery site.

The invention of this disclosure further provides for the manipulation and firing of the surgical stapling instrument from its rearward end with either hand during the course of a surgical operation.

The semi-disposable surgical stapler of this invention, particularly useful in intralumenal anastomosis, comprises upper and lower elongate jaws that accomodate, in frame members, respectively, a staple cartridge assembly and an anvil. Tissue is gripped between the jaws. A slider assembly is moved by a pusher bar means longitudinally relative to the jaws to eject a plurality of linear rows of staples, from a staple holder, on either side of the longitudinal center of the anvil. The knife blade, optionally included with the slider assembly, travels along the longitudinal center of the anvil to sever the tissue between the spaced rows of staples as the staples are sequentially ejected from the staple holder. The slider assembly, including the optional knife blade, is retracted by the pusher bar means to its initial position in the upper elongate frame member for replacement, together with an integral loaded staple holder, for the performance of further operation procedures involving stapling.

The stapler could alternatively be constructed having an integral glider assembly so that only the staple holder need be replaced for the performance of further operation procedures.

In one preferred procedure, two evenly spaced, linear, double rows of staples are placed in an internal body organ. The instrument comprises two aligned, elongate jaw members. The upper jaw contains a staple holder, fashioned to eject the staples, while the lower jaw member supports an anvil, which, in use, is aligned with the rows of staples to permit correct staple closing. A slider assembly, optionally including a knife blade, moves longitudinally through the staple holder, as it is pushed by a pusher bar means, sequentially ejecting the staples into the tissue. When employed, the knife blade places a longitudinal cut between the two double rows of staples.

In accordance with the invention, the need for local support means, such as shoes, in the elongate jaws of a surgical stapling instrument, is eliminated by use of a pusher bar means of the kind described that enters from the rearward openings in the upper and lower frames and which slidably moves along the frame members to effect the action of the slider assembly of the staple cartridge assembly.

In a preferred embodiment, the pusher bar means is a rigid member having connected upper and lower cross sections that fit slidably in passageways in the upper and lower elongate frame members, respectively, when the frames are closed. When the pusher bar means is urged forward to operate the stapler it travels longitudinally along the passageways.

The pusher bar means is so shaped as to allow for easy insertion thereof into the upper and lower elongate frame passageways, to allow for easy opening and closing of the instrument, and to aid in keeping the elongate upper and lower jaws properly aligned and free from distortion.

By utilizing the pusher bar means of this invention to effect the movement of the slider assembly of the staple cartridge assembly, the need for laterally extending projections of the slider assembly to effect movement thereof is eliminated. Thus, the slider assembly can be contained within the upper frame. This in turn allows portions of the bottom side of the upper elongate frame to rest against respective portions of the top side of the lower elongate frame. This contact between the upper and lower elongate frames provides significant structural support to resist vertical separation and lateral distortion of the elongate upper and lower jaw members, thus eliminating the need for support shoes to provide local support in the jaws. It has been found that the contact between the upper and lower elongate frames results in a substantially fully supported beam in both the elongate upper and lower jaws. Because support shoes are not needed in the jaws, the stapling instrument of this invention can be used without a knife blade, thus making use of a knife blade optional in accordance with the needs of the surgeon in performing the operation.

Forces generated in the elongate upper and lower jaw members urge the upper and lower elongate frame members rearward of the jaws to deflect towards each other. However, since portios of the upper and lower elongate frame members are already in contact, they experience substantially no deflections. Accordingly, when the pusher bar travels through the passageways in the upper and lower elongate frame members, it experiences no compressive or tensile forces and is free to glide therethrough.

The elimination of the need for support shoes in the jaws of the surgical stapler of this invention further allows for minimization of the size of the jaws, thereby facilitating manueverability of the stapler in and about the surgery site.

Placement of the entire staple cartridge assembly, including the slider assembly, within the upper elongate frame member has the added effect of eliminating up or down positions so that the stapler can be held in either hand without concern for orientation. Further, by use of the pusher bar means, the instrument can be operated with a single hand. The upper and lower elongate frame members may also be readily opened or closed with one hand.

Because of the semi-disposable nature of the surgical stapling instrument of this invention, it need not be discarded after each staple ejection step but can be used repeatedly by replacing the exhausted staple holder with a loaded one. This serves to reduce the cost of the surgery relative to the use of fully disposable models. Further, since the knife blade of the stapler of this invention is optional—unlike in prior art disposable and semi-disposable units—the use of sterilizable surgical staplers will not be necessary when the knife blade is not needed. This too serves to reduce the cost of the operation.

The fully disposable portion of the stapler instrument of this invention, comprising the staple holder and the slider assembly, may be removed from the instrument by retraction of the slider assembly to its original position in response to a rearward urging of the pusher bar means. In a preferred embodiment, the same motion that lifts the disposable staple cartridge assembly out of the elongate upper frame member disconnects an integral slider assembly from the pusher bar means. Both the staple holder and slider assembly may then be replaced with a fresh unit. Separable connecting means for assuring the concerted movement of the slider assembly and pusher bar means preferably comprises a ball-and-socket unit, with the ball member comprising the rearward extension of the slider assembly and the socket member comprising a forward extension of the pusher bar means.

The knife blade, when employed. is a component of the slider assembly, so that a fresh blade is available with each new staple cartridge assembly.

In order to prevent premature, accidental ejection of the staples, a detent assembly is preferably provided. The detent assembly is comprised of a receiving track and a peg received therein that cooperate to keep the pusher bar means and slider assembly in their retracted positions, but which allow for the pusher bar means, and thus the slider assembly, to be moved forward when sufficient force is applied. The receiving track is located on the underside of the top panel of the upper elongate frame member and extends longitudinally thereon. The peg projects from the top side of the pusher bar means. The receiving track has two opposed, inwardly projecting nipples that narrow the channel at a designated point so as to hinder longitudinal passage of the peg. The peg, and thus the pusher bar means, can be made to move forward past the nipples by applying a sufficient force to the pusher bar means.

The surgical stapling instrument of this invention can be manipulated, placed and locked with only one hand. It is preferably operated from the rear portions of the upper and lower elongate frame members, employing rests for two fingers and the thumb of either hand, thus providing a simplified control while freeing one hand of the surgeon for other tasks.

In the stapler of this invention, thus, the jaws and frames can be made of light-weight, simply configured, economic materials of construction, so that an instrument designed in accordance with the invention lends itself to manufacture in light-weight, inexpensive materials suitable for use in a disposable instrument.

These and other objects of the invention will become apparent from the following detailed description of a preferred embodiment, considered together with the drawings.

BRIEF DESCRIPTION OF THE DRAWINGS

The following drawings are included as illustrative, without limitation, of a preferred embodiment of the invention of this disclosure.

FIG. 1 is a perspective view of a preferred embodiment of a surgical stapling instrument according to the invention, with the jaws closed;

FIG. 2 is a perspective view of a staple cartridge assembly of the instrument of FIG. 1.

FIG. 3 is a side view of the instrument of FIG. 1 with the pusher bar means in its pre-staple ejection position.

FIG. 4 is a side view of the instrument of FIG. 1 with the pusher bar means in its post-staple ejection position.

FIG. 5 is a side view of the instrument of FIG. 1, with the handles removed, in the open condition.

FIG. 6 is a side view of the instrument of FIG. 1, with the handles removed, in the closed condition.

FIG. 7 is a bottom view of the upper elongate frame member of the instrument.

FIG. 8 is a side view of the upper elongate frame member of the instrument.

FIG. 8a is a sectional view taken from line A—A of FIG. 8.

FIG. 8b is a sectional view taken from line B—B of FIG. 8.

FIG. 8c is a sectional view taken from line C—C of FIG. 8.

FIG. 9 is a side view of the lower elongate frame member of the instrument.

FIG. 9a is a sectional view taken from line A—A of FIG. 9.

FIG. 9b is a sectional view taken from line B—B of FIG. 9.

FIG. 9c is a sectional view taken from line C—C of FIG. 9.

FIG. 10 is a top view of the locking lever of the instrument as shown in FIG. 1.

FIG. 11 is a side view of the pusher bar means of the instrument in FIG. 1.

FIG. 11a is a sectional view taken from line A—A of FIG. 11.

FIG. 12 is a rear view of the instrument, as shown in FIG. 3, excluding the pusher bar means.

FIG. 13 is a top view of the lower elongate frame member of the instrument as shown in FIG. 1.

FIG. 14 is a bottom view of the staple cartridge assembly as shown in FIG. 2.

FIG. 15 is a top view of an anvil member.

FIG. 16 is a side view of the anvil member of FIG. 15.

FIG. 17 is a sectional view taken along line 17—17 of FIG. 15. FIG. 17 also shows a sectional view of the anvil member situated on the elongate lower jaw member.

FIG. 18 is a side view of the instrument in the open condition.

DESCRIPTION OF THE PREFERRED EMBODIMENT

In a preferred embodiment of the semi-disposable stapler instrument of this invention, the instrument may generally be characterized as comprising:

(a) an upper elongate frame member having forward, intermediate, and rear sections, said forward section being an elongate upper jaw member, for receiving a staple cartridge assembly;

(b) a second lower elongate frame member, having forward, intermediate, and rear sections, said forward section being an elongate lower jaw member, describing an anvil section, characterized as having a central longitudinal opening;

(c) hinge means, attaching the upper and lower elongate frame members at their respective rearward extremeties so that a staple holder and said anvil section are positionable in direct opposition;

(d) a pusher bar means, slidably received at the rearward extremity of the respective rear sections of the upper and lower elongate frame members, removably attached to a slider assembly;

(e) a locking means, for substantially maintaining said upper and lower elongate frame members, in cooperation with said hinge means, in fixed relative position; and (f) a detent means to protect against premature ejection of staples.

In use, the upper elongate frame member receives a removable staple cartridge assembly comprising a staple holder and a slider assembly integral therewith, said staple holder inserted into said forward and intermediate sections of, and said slider assembly inserted into said rear section of, said upper elongate frame member, said slider assembly being slidably accomodated within the rear section of the upper elongate frame member.

One preferred embodiment of this invention is set forth herewith, with references to the drawings, and without limitation upon the scope of the invention.

A preferred embodiment 100 of the instrument of the invention includes an upper elongate frame member 10 and a lower elongate frame member 30. The forward end of upper frame 10 defines an elongate upper jaw member 15, while the forward end of the lower frame 30 defines an elongate lower jaw member 35. The instrument 100 comprises a hinge means 66 comprised of a rear pivot bar 60 at the rear end of lower elongate frame member 30 and a rear jacket 61 at the rear end of upper elongate frame member 10. Rear pivot bar 60 is received in notches 62 of the jacket 61.

The instrument 100 further comprises a locking means 68 for substantially maintaining said upper and lower elongate frame members in fixed relative position, described as follows: Lower elongate frame member 30, intermediate its length, has a forward pivot bar 51, the ends of which fit in complementary openings 56 (see FIG. 10) defined in a bifurcated locking lever 55, having parallel side walls 63 and a bottom panel 66. Upper elongate frame member 10 has, intermediate its length, a forward jacket 70 having slots 72. Locking lever 55 has laterally projecting lugs 52 that fit into openings 57 defined in locking lever 55. The locking means 68 and the hinge means 66 cooperate to open and close the instrument 100. More specifically, the lugs 52 cooperate with slots 72 of forward jacket 70 to close the instrument. By pivoting locking lever 55 counterclockwise to cause projecting lugs 52 to slide into slots 72, locking lever 55 can be used to rotate the frames 10, 30 toward each other about the rear pivot bar 60 between the open condition shown in FIG. 5 and the closed condition shown in FIG. 6. The location of projecting lugs 52 on locking lever 55 respective to slots 72 is such as to lock the jaws 15, 35 in the closed condition. Likewise, the instrument 100 can be caused to be in the open condition by rotating locking lever 55 clockwise.

Locking lever 55 also has a stop member 64 that is substantially perpendicular to, and situated between, side walls 63. Either end of stop member 64 is received in complementary openings 68 defined in locking lever 55 (as shown in FIG. 10). Stop member 64 prevents locking lever 55 from rotating beyond a desired angle in the clockwise direction when the lever 55 is allowed to hand free when the instrument 100 is in the open condition.

For use, a disposable staple cartridge assembly 80 (FIGS. 2 and 14) is inserted into upper elongate frame member 10. Such disposable staple cartridges are well known in the art. By way of example and in order to describe the preferred embodiment of the disclosed invention, reference will be made to a unitary disposable staple cartridge assembly wherein the slider assembly is an integral member of the staple cartridge assembly. In some staple cartidge assemblies, such as that disclosed in U.S. Pat. No. 3,499,591, incorporated herein by reference, the slider assembly is initially not connected to the staple holder but is of design to be slidably engaged therewith in operation of the surgical stapling instrument. Such staple cartridge assemblies function under the same principles as the unitary assembly herein described, with the exception that the slider assembly can disengage from the staple holder. The invention of this disclosure is not limited to the unitary staple cartridge assembly herein described by way of the preferred embodiment. The invention may, in the alternative, be comprised of a slider assembly such that the slider assembly can be reused when fresh staple holders are inserted into the instrument.

Disposable staple cartridge assembly 80 comprises: a staple holder 81, further comprising a body containing longitudinal rows of staples: a nose guide 99: a positioning ridge 98; a central longitudinal slot 102; a slider assembly 82; and a collar 83. Slider assembly 82 further comprises a central knife carrier 85, laterally spaced slider bars 84 and 86 located to either side of knife carrier 85, longitudinal slots 92 and 94, a connecting strip 93 and an end cap assembly 88. The end cap assembly 88 has a rearwardly projecting clip 91, which in the preferred embodiment is a ball member, that engages a pusher bar means 110. By means of connecting strip 93, the slider bars 84, 86 are maintained in fixed parallel relation to each other. It is noted that the slider assembly disclosed in U.S. Pat. No. 3,499,591, incorporated herein by reference, does not have a connecting strip. Instead, the slider bars of that disclosure are maintained in fixed relation by means of a spacer 270 as shown in FIG. 28 of that disclosure.

The slider bars 84, 86 terminate at their forward ends in slightly offset inclined slider bar cams (not shown—see cams 28, 30 shown in FIG. 29, and pusher cam 228 shown in FIG. 23, of U.S. Pat. No. 3,499,591), and knife carrier 85 includes an inclined knife 90 situated just to the rear of slider bar cams. The slider bar cams are slidably accomodated in longitudinal slots 92, 94 of staple holder 81. Each slot 92, 94 further accomodates a row of staple pushes (not shown—see drive member cam 196 in FIG. 23 of U.S. Pat. No. 3,499,591) that are pushed downward by the forward ends of the slider bar cams, thereby effecting ejection of the individual staples. The rear ends of the slider bars 84, 86, connecting strip 93, and knife carrier 85 are mounted in a known manner to the end cap assembly 88.

Slider assembly 82 is integral with staple holder 81. Collar 83, which is concentrically mounted on staple holder 81, prohibits disengagement of slider assembly 82 from the staple holder 81 by not allowing inclined knife 90, slidably positioned in central longitudinal slot 102, from being rearwardly removed from said slot.

An anvil member 95 having a central longitudinal opening 96, and having staple shaping depressions 97 in its outer surfaces complementary to the position of the individual staples in staple holder 81, is mounted on elongate lower jaw member 35. See FIGS. 13 and 17. Alternatively, the staple shaping depressions 97 can be formed directly on the surface of elongate lower jaw member 35.

The instrument 100 is inserted into a patient's body and manipulated so that the tissue to be sutured and optionally cut is placed between jaws 15, 35, an incision to recieve one of the jaws having previously been made in the tissue as necessary. Jaws 15, 35 are then closed and locked, by means of locking lever 55, to grip the tissue firmly between the opposing staple holder 81 and anvil member 95.

Slider assembly 82, which is initially in a rearward prefiring position (shown in FIG. 2) relative to jaws 15, 35, is then pushed forward by means of pusher bar 110. The slider bar cams cooperate with the camming surface of each individual staple pusher in turn to force the staples successively from staple holder 81, through the gripped tissue and into contact with the anvil depressions 97, which thereby, in cooperation with the cams force the staples closed. Each slot 92, 94 contains one row of staple pushers each of which carries two mutually staggered rows of staples, so that in all, four staple rows are formed in the gripped tissue. The inclined knife 90, which, when used, trails the slider cams slightly and rides in central longitudinal slot 102 in the staple holder 81 tissue along a line between the and in longitudinal slot 96 in anvil member 95, cuts the gripped tissue along a line between the two pairs of staggered staple rows.

The ejection and closing of the staples generates forces tending to pry the elongate upper and lower jaw members 15, 35 apart, and also tending to distort the jaws 15, 35 laterally. If stapler 100 is to be manufactured of relatively light-weight materials, it is necessary to design the stapler instrument such that the vertical separation and lateral distortion of jaws 15, 35 is kept within an acceptable level. To this end, upper and lower elongate frame members 10 and 30 are designed so as to afford maximum support to jaws 15, 35, the preferred embodiment of which is described below.

Upper elongate frame member 10 has three sections—forward section 11, intermediate section 12, and rear section 13. Forward section 11 defines elongate upper jaw member 15. As will be discussed, upper elongate frame member 10, and thus its three sections, in the preferred embodiment, has several cross-sectional shapes along its length. Upper elongate frame member 10 is comprised of a top panel 21 of substantially uniform width and thickness that extends the full length of frame 10. Top panel 21 thus serves as the top panel for all of the upper sections 11, 12 and 13, and thus defines a common portion of all of the cross-sectional shapes along the length of upper frame 10. Upper elongate frame member 10 is also comprised of side panels 22 and 23 of substantially uniform height and thickness (except as explained below) that extend the full length of frame 10. Side panels 22, 23 extend substantially perpendicular to and downward from either lateral side of top panel 21. Like top panel 21, side panels 22, 23 are common to the forward, intermediate and rear sections. Side panels 22, 23 are of substantially uniform height along rear section 13, intermediate section 12 and the rearward portion of forward section 11. As shown in FIGS. 7 and 8, side panels 22 and 23 are of a slightly shorter height along the forward portion of forward section 11 than they are along the remaining portions of upper elongate frame member 10, thereby defining a shoulder 14 in the upper frame 10.

The instrument 100 has a locking point 65. Locking point 65 is defined by the location of the central axis of the laterally projecting lugs 52 when the instrument 100 is in the closed condition. Forward section 11, describing elongate upper jaw member 15, is that portion of upper elongate frame member 10 that extends from the forward end of frame 10 rearward to the locking point 65. Forward section 11 has along its length two substantially U-shaped cross-sections 16 and 17, as shown in FIGS. 8a and 8b, respectively. The forward portion of forward channel 11, which extends rearward from the forward end of upper elongate frame member 10 to the rear end of shoulder 14, is defined by top panel 21, downwardly extending side panels 22, 23, and shoulder 14. The forward portion of forward section 11 thus defines the substantially U-shaped cross-section 16. The forward portion of forward section 11 having cross-sectional shape 16 corresponds in length to that length of the portion of staple holder 81 from which staples are ejected. The remaining portion of forward section 11, i.e. the portion extending from the rear end of shoulder 14 rearward to the locking point 65, is defined by top panel 21 and side panels 22, 23. This rearward portion of forward section 11 thus defines the substantially U-shaped cross-section 17.

The staple holder 81 is generally similar to the known type described in the aforementioned U.S. Pat. No. 3,499,591 as to the number of staple rows and the design and location of the individual staple pushers. For a fuller description of these elements and the manner in which the slider bar cams cooperate with the individual staple pushers to eject the staples, reference may therefore be made to that patent.

In use, staple cartridge assembly 80 is inserted into upper elongate frame member 10. The staple cartridge assembly 80 has a solid nose guide 99 that, when in place, projects forward from the forward most end of elongate upper jaw member 15 (forward section 11). In addition to other features of the stapler cartridge assembly which will be discussed, solid nose guide 99 is shaped to facilitate insertion of elongate upper jaw member 15 into and about the surgery site. The portion of staple holder 81 that is positioned in forward section 11 fits snugly therein such that the top side of staple holder 81 is substantially flush with the bottom side of top panel 21, and the bottom side of staple holder 81 lies in substantially the same horizontal plane as the bottom ends of side panels 22, 23 of upper elongate frame member 10.

The nose guide 99 is wider than staple holder 81, to which it is attached, thereby providing a means for maintaining the longitudinal positioning of staple cartridge assembly 80 when inserted into upper elongate frame member 10. Positioning ridge 98 of staple cartridge assembly 80, which is slidably received in notch 27 of side panel 22 (see FIG. 7), acts in concert with nose guide 99 to maintain the longitudinal position of the staple cartridge assembly 80.

It should also be noted that the top side of collar 83 of staple cartridge assembly 80 may project upward from the otherwise substantially flat top surface of staple holder 81. To accomodate the upwardly projecting portion of collar 83, the bottom side of top panel 21 of the preferred embodiment has a complementary substantially rectangular depression 28. We note that this and other specific features of the preferred embodiment are provided to accomodate details of the staple cartridge assembly. Such features are not meant to limit the invention herein disclosed and claimed.

Intermediate section 12 of upper elongate frame member 10 is that portion of frame 10 that extends from locking point 65 rearward to the rear end of staple holder 81 when inserted into upper elongate frame member 10. Intermediate section 12 is defined by top panel 21 and side panels 22, 23. Intermediate section 12 thus has a substantially U-shaped cross-section 17—the same cross-sectional shape as the rearward portion of forward section 11. It is noted that the receiving notch 27 of side panel 22 and the substantially rectangular depression 28 of top panel 21, both of which are located in intermediate section 12 cause, at their respective locations, minor variations in the otherwise substantially uniform cross-sectional shape 17 of intermediate section 12.

Rear section 13 of upper elongate frame member 10 is that portion of upper frame 10 that extends rearward from the rear end of intermediate section 12 to the rear end of upper elongate frame member 10. Rear section 13 is defined by top panel 21, side panels 22, 23 and two flanges 19 and 20. Flanges 19 and 20 extend substantially perpendicular to and inward from the bottom ends of side panels 22, 23 and are substantially parallel to top panel 21. Rear section 13 thus has a cross-sectional shape 18 that defines a substantially T-shaped passageway 75 as shown in FIG. 8c. The bottom sides of flanges 19, 20 are in the same horizontal plane as the bottom ends of side panels 22, 23. In the preferred embodiment, at the rear end of rear section 13, a small length of the flanges 19, 20 is removed to facilitate insertion of and initial movement of pusher bar means 110 (see FIG. 8).

When staple cartridge assembly 80 is inserted into upper elongate frame member 10, the slider assembly 82 is slidably accomodated within rear section 13.

Lower elongate frame member 30 also has three sections—forward section 31, intermediate section 32 and rear section 33. Forward section 31 defines elongate lower jaw member 35. Lower elongate frame member 30 has substantially the same width as upper elongate frame member 10. The forward, intermediate and rear sections of lower elongate frame member 30 correspond in substantially direct opposition with the forward, intermediate and rear sections of upper elongate frame member 10, respectively, when the instrument is positioned in the closed condition. For example, forward section 11 of upper elongate frame member 10 begins at the forward end of upper frame 10 and extends rearward to locking point 65. Likewise, forward section 31 of lower elongate frame member 30 begins at the forward end of lower frame 30 and extends rearward to locking point 65. In essence, the three sections of lower elongate frame member 30 are positioned directly below, and aligned with, the correspondingly-named sections of upper elongate frame member 10 when the instrument 100 is assembled.

Lower elongate frame member 30 is comprised of a bottom panel 36 of substantially uniform width and thickness that extends the full length of frame 30. Bottom panel 36 thus serves as the bottom panel for all of the lower sections 31, 32 and 33, and thus defines a common portion of the cross-sectional shapes along the length of lower elongate frame member 30. Lower elongate frame member 30 is also comprised of side panels 37 and 38 of substantially uniform height and thickness (except as explained below) that extend the full length of frame 30. Side panels 37, 38 extend substantially perpendicular to and upward from either lateral side of bottom panel 36. Like bottom panel 36, side panels 37, 38 are common to the forward, intermediate and rear sections. Side panels 37, 38 are of substantially uniform height along rear section 33 and intermediate section 32. As shown in FIG. 9, side panels 37, 38 are of a slightly shorter height along forward section 31 than they are along the other portions of lower frame 30.

Forward section 31, defining elongate lower jaw member 35, is that portion of lower frame 30 that extends from the forward end of frame 30 rearward to locking point 65. In addition to being comprised of bottom panel 36 and side panels 37, 38, forward section 31 is further defined by top panels 44 and 45 and interior support panels 46 and 47. Top panels 44, 45 extend substantially perpendicular to and inwardly from the top ends of side panels 37, 38 and are substantially parallel to bottom panel 36. Interior support panels 46, 47 extend substantially perpendicular to and downward from the inward ends of top panels 44, 45 and are substantially parallel to side panels 37, 38. The bottom sides of interior support panels 46, 47 rest upon the top side of bottom panel 36, thereby restraining top panels 44, 45 from experiencing any consequential downward deflection when downward forces are applied to those panels during stapling. Interior support panels 46, 47 define a longitudinal central opening 104, which, as will be discussed, accomodates both passage of inclined knife 90 and mounting of anvil member 95. The elements comprising forward section 31 define a cross-sectional shape 41 as shown in FIG. 9a.

The forward portion of elongate lower jaw member 35 (forward section 31) defines an anvil section 101 (see FIG. 13) that supports anvil member 95 (see FIGS. 15-17). The anvil member 95 has two anvil surfaces 108 and 109 with staple-shaping depressions or buckets 97, inner walls 127 and 128 and outer walls 129 and 130. These elements comprising anvil 95 are contiguously attached so as to define a member that is substantially complementary in shape to anvil section 101 as it is approached from its top side, and which can thus be matingly mounted thereon (see FIG. 17). As such, outer walls 129, 130 are substantially parallel to side panels 37, 38, and anvil surfaces 108, 109 are substantially parallel to panels 44, 45. Inner walls 127, 128, which are connected at their respective longitudinal lower ends are slightly angled to provide a friction fit of anvil member 95 onto anvil section 101.

Anvil member 95 has a longitudinal central opening 96 that is received between the interior support panels 46, 47 of elongate lower jaw member 35. Longitudinal central opening 96 allows passage of the vertically extending inclined knife 90 (when used). The outer walls 129, 130 each have depressions 126 which are received in complementary depressions (not shown) in the side panels 37, 38 of lower jaw 35 when the anvil member 95 is in place at the proper longitudinal location on anvil section 101, with the staple shaping depressions 97 accurately aligned with the individual staples in staple holder 81.

While the instrument 100 as described includes an anvil member 95 which matingly mounts on elongate lower jaw member 35, it is also possible, in the alternative, particularly for a low-cost disposable instrument, to dispense with attachable anvils and to form the staple shaping depressions directly in the surfaces of top panels 44, 45 of elongate lower jaw member 35 at anvil section 101. In such case, the longitudinal central opening 104 allows passage of the inclined knife 90 (when used). It is also noted that if a knife blade is never desired, the lower jaw 35 and the anvil member 95 can be designed without central longitudinal openings 104 and 96, respectively.

The forward portion of elongate lower jaw member 35 also accomodates a guidance nose 107. Guidance nose 107 is longitudinally slidably received by lower jaw 35 at its forward end. Guidance nose 107 facilitates insertion of the lower jaw into and about the surgery site.

Intermediate section 32 of lower elongate frame member 30 is that portion of frame 30 that extends from locking point 65 rearward to the rear end of staple holder 81, i.e. the correspondingly rearward end of intermediate section 12 of upper elongate frame member 10. Intermediate section 32 is defined by side panels 37, 38, bottom panel 36, top panels 48 and 49 and interior support panels 53 and 54. Intermediate section 32 has a cross-sectional shape 42, as shown in FIG. 9b, which is similar to cross-sectional shape 41 of forward section 31. The side panels 37, 38 are slightly taller along intermediate section 32 than they are along forward section 31. Top panels 48, 49 extend perpendicular to and inwardly from the top ends of side panels 37, 38.

Interior support panels 53, 54 extend perpendicular and downward from the inward most ends of top panels 48, 49. The bottom sides of interior support panels 53, 54 are substantially flush with the top side of bottom panel 36. The space between interior support panels 53, 54 defines a longitudinal central opening 105 that is continuous with longitudinal central opening 104 of forward section 31. Longitudinal central opening 105 accomodates passage of inclined knife 90.

Just as the top side of detent band 83 of slider cartridge assembly 80 may project upward from the otherwise substantially flat top surface of staple holder 81, the bottom side of detent band 83 may project downward from the otherwise substantially flat bottom surface of staple holder 81. Thus, it may project below the bottom most horizontal plane of upper frame 10. To accomodate the downwardly projecting portion of collar 83, the top sides of top panels 48, 49 have complementary substantially rectangular depressions 74. Again, this specific feature of the preferred embodiment is described only because it is necessary given the staple cartridge assembly herein disclosed by way of example. Such features may not be necessary depending on the design of the staple cartridge assembly used.

Rear section 33 of lower elongate frame member 30 is that portion of lower frame 30 that extends rearward from the rear end of intermediate section 32 to the rear end of lower frame 30. Rear section 33 is comprised of bottom panel 36, side panels 37, 38 and two flanges 58 and 59. Flanges 58, 59 extend substantially perpendicular to and inwardly from the top ends of side panels 37, 38. Rear section 33 thus has a cross-sectional shape 43 as shown in FIG. 9c, defining a substantially T-shaped passageway 76. The top sides of flanges 58, 59 lie substantially in the same horizontal plane as the top ends of side panels 37, 38. At its rear end, rear section 33 has a bevel 67. When the stapling instrument 100 is assembled, bevel 67 allows the upper and lower elongate frame members to be rotated at hinge means 66 without interference from pusher bar means 110 when it is in the retracted position; bevel 67 also facilties forward movement of the pusher bar means.

The top sides of top panels 48, 49 of intermediate section 32 lie in substantially the same horizontal plane as the top sides of flanges 58, 59 of rear section 33, such that the top side of lower elongate frame member 30 is substantially horizontal along the length of the intermediate and rear sections.

In the preferred embodiment, a bend is induced in the lower elongate frame member 30 where the forward and intermediate sections 31, 32 meet so that the longitudinal axis of forward section 31 will be slightly angled relative to the longitudinal axis of the remainder of lower elongate frame member 30 (see FIG. 6). The induced angle is such that the forward end of section 31 will lie in a plane substantially at or adjacent to the horizontal plane defined by the bottom side of staple holder 81 when the instrument 100 is in the closed condition. When the stapling instrument 100 is in use, and the tissue is clamped between the elongate upper and lower jaw members, the forces generated by the tissue and the operation of the stapler will cause the forward end of lower jaw 35 to deflect slightly downward to overcome the induced angle so that the top side of the lower jaw 35 will be substantially horizontal, and thus substantially parallel to the bottom side of staple holder 81, thereby facilitating uniform staple closure.

When the components of the invention of this disclosure are assembled, and the frames 10, 30 are caused to be in the closed condition, i.e. the projecting lugs 52 on locking lever 55 are locked into slots 72 of forward jacket 70, the bottom sides of the intermediate and rear sections of the upper frame 10 will be in substantial contact with the top sides of the intermediate and rear sections of the lower frame 30, respectively. More specifically, the bottom ends of side panels 22, 23 of upper intermediate section 12 will lie substantially flat against the top sides of top panels 48, 49 of lower intermediate section 32. Likewise, the bottom sides of flanges 19, 20 of upper rear section 13 will lie substantially flat against the top sides of flanges 58, 59 of lower rear section 33. This contact along the intermediate and rear sections of the upper and lower elongate frame members restricts those sections of the frames from experiencing any inward vertical deflection when forces are generated at the jaws. It is believed that the combination of the contact along the frames in cooperation with the locking means 68 causes the upper and lower jaws to behave as fixed beams, thereby substantially reducing the amount of deflection that would be experienced in the jaws if, instead, the frame members were allowed to experience inward vertical deflections.

While the upper and lower elongate frame members have been herein described as having particular section lengths and shapes, it is also within the scope of the present invention for the frames to be designed differently, so long as sufficient contact may be achieved along portions of and between the frame members, so as to restrict deflections in the elongate jaw members to acceptable levels. For example, projections extending downward from the upper elongate frame member could supply the necessary contact between the upper and lower elongate frame members.

Staple ejection is effected by a forward movement of a pusher bar means 110 that is slidably received at the rear ends of upper elongate frame member 10 and lower elongate frame member 30. Pusher bar means 110 has a substantially I-shaped cross-section 112 as shown in FIG. 11a. Pusher bar 110 is comprised of a substantially rectangular upper tram 114, a substantially rectangular lower tram 116, and a substantially rectangular joining tram 115 that rigidly affixes upper tram 114 in relation to lower tram 116. The vertical spacing between the trams 114 and 116 is substantially equal to the vertical spacing between the passageways 75 and 76 in the upper and lower rear sections 13 and 33, respectively, when the upper and lower elongate frame members 10 and 30 are locked together in the closed condition. As shown in FIG. 12, when the upper and lower frames 10 and 30 are locked together, the generally T-shaped passageways 75 and 76 meet to form a single passageway having a substantially I-shaped cross-section. The substantially I-shaped cross-section 112 of pusher bar means 110 is of substantially the same size and shape as the substantially I-shaped passageway formed by passageways 75 and 76, so that pusher bar means 110 fits in passageways 75 and 76 with minimal clearance to allow substantially friction-free passage of pusher bar means 110 along the passageways 75 and 76.

Because the size and shape of pusher bar means 110 prevents the pusher bar from moving either vertically or laterally in its respective passageways 75 and 76, the pusher bar means 110 and the passageways 75 and 76 cooperate to resist both vertical separation and lateral misalignment of the jaws 15, 35 during stapling.

Pusher bar means 110 has an engaging beam 111 that extends forward from, and is connected to upper tram 114. Engaging beam 111 has a substantially rectangular cross-section substantially equivalent to that of upper tram 114. Engaging beam 111 has at the underside of its forward end a socket 122 that engages clip 91 of slider assembly 82 when staple cartridge assembly 80 is inserted into the instrument 100. In the preferred embodiment, the clip 91 and socket 122 forms a ball-and-socket connection. It is noted that a variety of separable connecting means are known and that the invention of this disclosure is not limited to the ball-and-socket arrangement herein described.

Engaging beam 111 also has a detent pin 117 that projects upward from the top side of upper tram 114. When movement of the pusher bar means 110 is effected, detent pin 117 travels along a receiving track 120 in the underside of top panel 21 of rear section 13 of upper elongate frame member 10. Receiving track 120 has a pair of opposed inwardly projecting nipples 124 that restrain passage of detent pin 117 therebetween until sufficient force is applied to the pusher bar means 110. When engaging beam 111 is inserted into the rear opening of upper elongate frame member 10 and is caused to travel forward until detent pin 117 reaches the rear side of nipples 124, socket 122 on the forward end of beam 111 will be properly situated to receive clip 91 when the staple cartridge assembly 80 is inserted into the upper frame 10. So engaged, pusher bar means 110 and slider assembly 82 act in concert such that a forward movement of pusher bar means 110 effects the same forward movement in slider assembly 82. Similarly, retraction of pusher bar means 110 will retract slider assembly 82.

The nipples 124 of track 120 help to ensure that pusher bar means 110, and thus slider assembly 82, is not moved forward until a required force is applied to pass detent pin 117 between the nipples 124. This will help eliminate premature, accidental firing of the stapler. It should also be noted that when the pusher bar means 110 and slider assembly 82 are engaged, said engagement will prevent the pusher bar from sliding rearward (out of the instrument) since slider assembly 82, as previously described, is prevented by collar 83 from being disengaged from staple holder 81 when it is retracted.

Joining tram 115 and lower tram 116 are tapered at their forward ends, as shown in FIG. 11, to facilitate insertion of pusher bar means 110 into the rear ends of the upper and lower elongate frame members 10, 30.

While the instrument 100 has been herein described as a reusable stapler used with a disposable, separate staple cartridge assembly 80, it is also within the scope of the present invention for the staple cartridge assembly 80 to be formed as an integral part of upper frame 10, in which case the entire instrument 100 is disposed of after one use. It is also noted that the pusher bar means herein disclosed is not limited to use with disposable or semi-disposable surgical stapling instruments, but can also be used with re-useable surgical staplers.

The preferred embodiment 100 includes upper and lower handle members 132 and 134, as shown in FIG. 1, comprising upper and lower finger rests 133 and 135, a locking indicator means 140 and a release point 145. The bottom surface of upper handle member 132 is provided with a channel (not shown) that receives the rear and intermediate sections 12 and 13 of upper elongate frame member 10. Upper handle member 132 has at its upper rear extremity a projection providing a finger rest 133. The top surface of lower handle member 134 is provided with a channel (not shown) that receives lever 55 and which thereby receives the rear and intermediate sections 32 and 33 of lower frame 30 when lever 55 is rotated counterclockwise into the closed position. Lower handle member 134 has at its lower rear extremity a projection providing a finger rest 135. All of the exterior edges of upper and lower handle members 132, 134 may be tapered or rounded so as to reduce the possibility of pinching tissue during use of the stapling instrument.

As shown in FIG. 12, when the instrument 100 is in the closed condition, the upper and lower handle members 132, 134 are positioned so as to be imposed over the rear and intermediate sections of the elongate frame members.

The upper and lower handle members 132, 134 have a locking indicator means 140, comprised of clip 141 on lower handle 132 and a complementary depression 142 on the inner surface of upper handle 134, that provides both a sensation to the surgeon's hand and an audible click when the instrument is caused to be in the closed condition. Clip 141 has an embossment 143 that is received by depression 142 when lower handle member 134 (and thus lever 55) is rotated counterclockwise and lever 55 locks into the closed position. At the moment the locking action takes place, embossment 143 is received by depression 142. The click and sensation provided by the locking means 140 is an indicator to the surgeon that the stapler instrument 100 is locked and ready for staple ejection. The clip 141 can be easily disengaged from the depression 142 by applying inward pressure at the release point 145 and, at the same time, pushing lower handle member 134 away from upper handle member 132. This releasing pressure and motion can be supplied simply with the thumb of one hand. It is noted that a variety of means for providing the function of locking indicator means 140 are known, and so the claimed invention is not meant to be limited to the locking indicator means 140 herein described.

Pusher bar means 110 has at its rear end a thumb rest 123 having lips 125 at the upper and lower distal edges of the thumb rest. To eject staples when the stapler instrument 100 is in the closed condition, the surgeon places the thumb of either hand on thumb rest 123 and the ends of the index and forefinger (or any two fingers) of the same hand on the corresponding upper and lower finger rests 133, 135. Then, pusher bar means 110 is made to move forward as the surgeon moves the thumb towards the fingers in a syringe-like manner. The lips 125 help to ensure proper placement of the thumb on, and keep the thumb from slipping off of, the thumb rest 123. The instrument can be operated by either hand as there is no "right" or "left" orientation to either the pusher bar means 110 or the finger rests 133, 135. For the same reason, the instrument 100 has no "up" or "down" position, i.e. the instrument can be turned in any orientation and still be effectively operated by either hand.

The various components of the instrument 100 are assembled in the following manner. Forward and rear jackets 70 and 61 are fitted onto upper elongate frame member 10, suitable complementary locating means (not shown) being provided on the jackets 70 and 61 and upper frame 10 to align these elements longitudinally and to prevent relative movement of jackets 70 and 61 and upper frame 10 during staple ejection and handling of the instrument. Then, upper frame 10, with jackets 70 and 61, is fitted into upper handle member 132, suitable complementary locating means (not shown) being provided on the upper frame 10 and upper handle member 132 to align these elements longitudinally and to prevent relative movement of upper frame 10 and upper handle member 132 during staple ejection and handling of the instrument.

Next, the forward end of pusher bar means 110 is inserted from the rear into upper elongate frame member 10, with engaging beam 111 fitting in passageway 75 and detent pin 117 received in track 120; pusher bar 110 is moved forward along frame 10 until detent pin 117 reaches the rear side of nipples 124. Stapler cartridge assembly 80 is then inserted into upper elongate frame member 10, thereby engaging clip 91 of the slider assembly 82 with socket 122 of the engaging beam 111.

Lugs 52 are fitted into openings 57 of locking lever 55. Locking lever 55, with lugs 52, is then fitted into lower handle member 134, suitable complementary locating means (not shown) being provided on the lever 55 and lower handle member 134 to align these elements longitudinally and to prevent relative movement of lever 55 and lower handle member 134 during staple ejection and handling of the instrument.

Rear and forward pivot bars 60, 51 are then secured to lower frame 30, suitable locating means (not shown) being provided on the lower frame 30 to align these elements longitudinally and to prevent relative movement of pivot bars 60, 51 and lower frame 30 during staple ejection and handling of the instrument. Lever 55, with lower handle member 134, is then rotatably attached to forward pivot bar 51, said pivot bar 51 being fitted into openings 56 on lever 55.

Next, anvil member 95 is fitted onto lower jaw 35. Then, with the rear end of lower handle member 134 tilted downward (clockwise), as shown in FIG. 18, notches 62 of rear jacket 61 are engaged with pivot bar 60, completing the assembly of the instrument 100.

In use, the instrument 100 in the assembled, open condition is inserted into a body cavity so that tissue to be stapled is accepted between elongate upper and lower jaw members 15 and 35, and the instrument 100 is then locked by manipulation of lower handle member 134 (attached to locking lever 55) and cooperation of slots 72 with lugs 52. With tissue gripped between the jaws 15 and 35, with the instrument 100 in the closed condition a shown in FIG. 1, and with the surgeon's hand in place (thumb on thumb tab 123), the tissue is stapled and cut (if the knife blade is optionally used) in the manner described in the aforementioned U.S. Pat. No. 3,499,591 by pushing the pusher bar means 110 forward.

When stapling has been completed, the pusher bar means 110, and thus the engaged slider assembly 82, is retracted to the initial position. In this position, lower tram 116 is clear from passageway 76 in lower elongate frame member 30 so that lower handle member 134 can be pivoted at hinge means 66 to open the instrument 100.

With the instrument 100 in the open condition, the upper and lower elongate frame members 10 and 30 can be pivoted apart at hinge means 66, and a fresh staple cartridge assembly 80 can be placed into upper frame 10 to repeat the procedure if desired.

The pusher bar means 110, received in passageways 75 and 76, allows the top sides of the lower frame 30 along its rear section 33 and intermediate section 32 to meet the bottom sides of the upper frame 10 along its rear section 13 and intermediate section 12, respectively. This, in turn, provides significant structural support to the jaws 15 and 35 to resist jaw-opening forces that occur during stapling. In addition, because the pusher bar means 110 is a rigid member, it will be appreciated that during stapling, as the pusher bar moves along the passageways 75 and 76 with minimal clearance, it also provides some degree of both vertical and lateral support to the jaws 15, 35. As a result, the construction illustrated in this disclosure and the invention as claimed particularly lends itself to manufacturing the elongate upper and lower jaw members 15, 35 and the entire instrument 100 of relatively light weight disposable materials, although the construction is also suitable for use in instruments manufactured from heavier materials.

While only one preferred embodiment of the invention has been described in detail, the invention is not limited to the specific features described, and many modifications that will now be apparent to those skilled in the art are possible within the scope of the appended claims. Thus, while the invention has been particularly described in relation to surgical stapling, the invention is not limited to this application, but may also be applied to other fastening instruments having opposed jaws which require stabilization while fastening means are applied to matter gripped between the jaws. For example, the invention may be applied to instruments for applying certain types of surgical clips or to instruments for applying surgical fastening devices. Accordingly, the scope of the invention is to be limited not by details of the preferred embodiment described herein, but only by the appended claims.

We claim:

1. A surgical stapling instrument comprising:
   (a) an upper elongate frame member for receiving a staple holder, said upper elongate frame member further comprising a forward section defining an elongate upper jaw member;
   (b) a lower elongate frame member, said lower elongate frame member further comprising a forward section defining an elongate lower jaw member, said elongate lower jaw member comprising an anvil section;
   (c) hinge means, attaching said upper and lower elongate frame members at their respective rearward extremities, to enable said anvil section to be positioned directly opposed to said staple holder;
   (d) a locking means, for substantially maintaining said upper and lower elongate frame members in fixed relative position;
   wherein said upper and lower elongate frame members are in contact along substantially their entire lengths rearward of said elongate upper and lower jaw members when said upper and lower elongate frame members are locked in fixed relative position, whereby deflections of the elongate upper and lower jaw members are minimized.

2. The instrument of claim 1 wherein a staple cartridge assembly, comprising a staple holder and a slider assembly, is positionable in said upper elongate frame member, wherein in response to a forward movement of said slider assembly sequential ejection of staples from a staple holder may be effected.

3. The instrument of claim 2 further comprising a means for effecting said forward movement of said slider assembly.

4. The instrument of claim 3 wherein said means for effecting said forward movement of said slider assembly comprises a pusher bar, slidably receivable at the rearward extremity of the rear sections said upper and lower elongate frame members, separably connectable to said slider assembly.

5. The surgical stapling instrument of claim 4 wherein said pusher bar is configured to support said upper an lower elongate frame members thereby minimizing lateral deflections of said upper and lower elongate frame members.

6. The surgical stapling instrument of claim 4, further comprising upper and lower handle members imposed over a portion of said upper and lower elongate frame members in a fixed configuration when said locking means is in the locked condition, said upper and lower handle members further comprising finger rests thereby enabling the user to enlist a syringe-like action to effect a forward movement of said pusher bar.

7. The instrument of claim 2, wherein after said sequential ejection of staples, said slider assembly can be retracted to permit unlocking of said upper and lower elongate frame members, thereby allowing removal of said staple cartridge assembly, further allowing installation of another staple cartridge assembly.

8. The surgical stapling instrument of claim 2 wherein said anvil section has a longitudinal central opening.

9. The surgical stapling instrument of claim 8 wherein said staple cartridge assembly additionally includes a knife blade, wherein said knife blade can be caused to travel through said longitudinal opening in said anvil section, thereby enabling the severance of substance being stapled.

10. The instrument of claim 1 further comprising a slider assembly slidably associated with said upper elongate frame member.

11. The instrument of claim 1 wherein said upper elongate frame member further comprises a staple cartridge assembly, said staple cartridge assembly further comprising a staple holder and a slider assembly.

* * * * *